(12) United States Patent
Callegaro et al.

(10) Patent No.: US 8,765,714 B2
(45) Date of Patent: Jul. 1, 2014

(54) SULPHATED HYALURONIC ACID FOR TREATING DEGENERATIVE OSTEOARTHRITIS

(75) Inventors: Lanfranco Callegaro, Abano Terme (IT); Davide Renier, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 13/410,227

(22) Filed: Mar. 1, 2012

(65) Prior Publication Data

US 2012/0165254 A1    Jun. 28, 2012

Related U.S. Application Data

(62) Division of application No. 12/302,511, filed as application No. PCT/EP2007/003920 on May 3, 2007, now abandoned.

(30) Foreign Application Priority Data

May 31, 2006   (IT) .............................. PD2006A0219

(51) Int. Cl.
- *A61K 31/727* (2006.01)
- *A01N 43/04* (2006.01)
- *A61K 31/715* (2006.01)

(52) U.S. Cl.
USPC .............................................. 514/56; 514/54

(58) Field of Classification Search
CPC ........................... A61K 31/737; A61K 31/728
USPC ..................................................... 514/54, 56
See application file for complete search history.

(56) References Cited

U.S. PATENT DOCUMENTS

| | | | |
|---|---|---|---|
| 5,872,109 A | 2/1999 | Akima et al. | |
| 6,579,978 B1 | 6/2003 | Renier et al. | |
| 6,833,363 B2 | 12/2004 | Renier et al. | |
| 6,924,273 B2 * | 8/2005 | Pierce | 514/54 |
| 2003/0060448 A1 | 3/2003 | Rivarossa et al. | |

FOREIGN PATENT DOCUMENTS

| | | | | |
|---|---|---|---|---|
| WO | WO 95/25751 | * | 9/1995 | ............. C08B 37/00 |
| WO | WO-00/61675 A1 | | 10/2000 | |
| WO | WO-00/78356 A1 | | 12/2000 | |
| WO | WO-2005/082433 A1 | | 9/2005 | |

OTHER PUBLICATIONS

Gutowska, A., Jeong, B., Jasionowski, M. (2001) Injectable Gels for Tissue Engineering. The Anatomical Record, vol. 263, p. 342-349.*
Freemont, A.J., Denton, J. (1991) "Non-inflammatory Arthopathies 1. Osteoarthritis" from Atlas of Synovial Fluid Cytopathology, vol. 18, p. 91-95.*
Mahajan, A., Verma, S., Tandon, V. (2005) Osteoarthritis. Journal of the Association of Physicians of India, vol. 53, p. 634-641.*
Hamilton et al., "The Response of Primary Articular Chondrocytes to Micrometric Surface Topography and Sulphated Hyaluronic acid-based Matrices," Cell Biol International 29(8):605-615 (2005).
Barbucci et al., "Immobilisation of Sulphated Hyaluronan for Improved Biocompatibility," 79(1-4):119-125 (2000).
Definition of "prevention" from the Institute for International Medical Education [online]. [Retrieved on Mar. 24, 2011]. Retrieved from the Internet <http://www.lime.org/glossary.htm. Published Feb. 2002, p. 1, 2, 26, 27 and 39.
"What is Osteroarthritis?" by U.S. Department of Health and Human Services, National Institute of Health, National Institute of Arthritis and Musculoskeletal and Skin Diseases, Sep. 2006.

* cited by examiner

*Primary Examiner* — Scarlett Goon
(74) *Attorney, Agent, or Firm* — Birch, Stewart, Kolasch & Birch, LLP

(57) ABSTRACT

This invention relates to oral and intra-articular formulations based on sulphated hyaluronic acid which are effective in the treatment of degenerative osteoarthritis.

7 Claims, 3 Drawing Sheets

Figure 1:
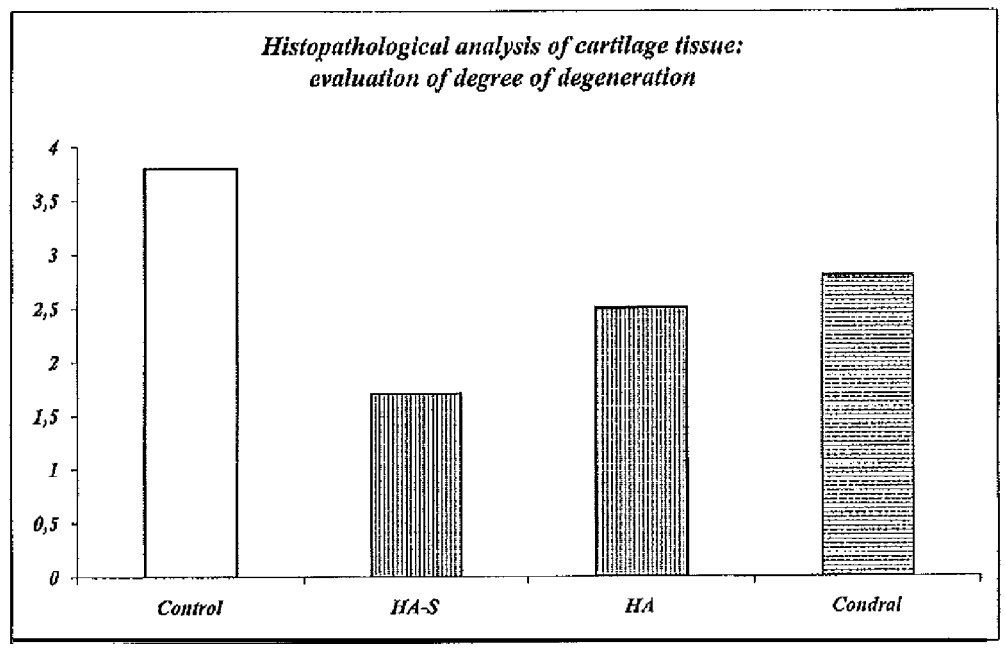

Degeneration scale:

0: none

1: slight

2: moderate

3: marked

4: very marked / serious

Structural integrity scale (Yoshimi et al., Clin Orthop, 1994, 298:296-304):

0: normal

1: slight surface irregularity

2: moderate surface irregularity

3: serious surface irregularity

4: cracks in transition zone

5: cracks in radial zone

6: cracks in calcified zone

7: loss of transition zone

8: loss of radial zone

9: loss of calcified zone

10: complete disorganisation

SULPHATED HYALURONIC ACID FOR TREATING DEGENERATIVE OSTEOARTHRITIS

This application is a Divisional of co-pending application Ser. No. 12/302,511 filed on Nov. 26, 2008, and for which priority is claimed under 35 U.S.C. §120; co-pending application Ser. No. 12/302,511 is the National Phase Under 35 U.S.C. §371 of PCT International Application No. PCT/EP2007/003920 filed on May 3, 2007, and which application claims priority of Application No. PD2006 A 000219 filed in Italy on May 31, 2006 under 35 U.S.C. §119; the entire contents of all are hereby incorporated by reference.

SUBJECT OF THE INVENTION

The present invention relates to oral and intra-articular formulations based on sulphated hyaluronic acid which are effective in the treatment of degenerative osteoarthritis.

FIELD OF INVENTION

Osteoarthritis (OA) is a very common disorder, characterised by progressive degeneration of the joint cartilage which thins and deteriorates following loss of the cellular and extracellular component, and can even disappear entirely. The causes of the disease are only partly clear. They basically seem to involve a series of processes triggered by a mechanical imbalance that affects the entire joint, for example after a trauma or mechanical stress. Inside the cartilage there is a delicate balance between destruction of the exhausted extracellular matrix and formation of intact matrix. All this depends largely on enzymes produced by the chondrocytes, a cellular component of joint matrix. In the event of an excessive or unbalanced load on the joint, an inflammatory situation arises. This triggers the release of inflammatory cytokines which, in turn, stimulate the chondrocytes to produce metalloproteases (MMP), enzymes responsible for cartilage destruction, thus altering the balance between synthesis and degradation of the extracellular matrix. The scientific literature also describes in detail the cell death processes which affect the chondrocytes when they come into contact with substances produced by the breakdown of the matrix (Cao et al., *Exp Cell Res,* 1999, 246:527-37).

In view of the factors described above, degenerative osteoarthritis can be defined as a chronic disease which normally occurs after an initial acute stage of inflammation, known as inflammatory osteoarthritis. The presence or absence of an inflammatory state in the joint (caused by cytokines and MMPs together with other substances) distinguishes the acute inflammatory stage of the disease (inflammatory osteoarthritis) from the chronic non-inflammatory stage (degenerative osteoarthritis). Degenerative osteoarthritis does not only occur as the chronic stage of inflammatory osteoarthritis, but also results from physiological aging of the joint cartilage.

The integrity of the extracellular matrix is therefore crucial to the survival of the chondrocytes, and consequently essential for healthy cartilage.

The cartilage matrix is a three-dimensional structure consisting of collagen molecules and aggregated complexes of proteoglycans, which in turn are formed by
  a skeleton of hyaluronic acid (HA),
  glycosaminoglycans (GAG) containing repetitive disaccharide units of glucosamine or galactosamine, which in turn carry negatively-charged carboxyls or sulphate groups, as a result of which the GAGs form long negatively-charged chains,
  polypeptides.

HA is a polysaccharide molecule with considerable viscoelastic properties. It is present in the joint cavities as a fundamental component of synovial fluid, where it acts as a lubricant and shock-absorbing agent, and protects the chondrocytes against the action of the inflammatory cytokines (Asari et al., *Arch Histol Cytol,* 1995, 58:65-76; Brun et al., *Osteoarthr Cartil,* 2003, 11:208-16; Stove et al., *J Orthop Res,* 2002, 20:551-5). HA, as such or in derivatised form, has long been used to treat degenerative osteoarthritis, either as a "viscosupplement" or a lubricant.

The various products include (by way of example) Hyalgan (HA purified from rooster combs according to EP 138572 B1), Synvisce (Hylan G-F20, namely HA crosslinked with formaldehyde and divinyl sulphone, as described in U.S. Pat. No. 4,713,448), and Artz® (HA with a MW of between 620 and 1200 KDa), which can only be administered by the intraarticular route.

The oral treatments according to the prior art involve the administration of sulphated GAGs such as glucosamine sulphate and chondroitin sulphate in association with HA and hydrolysed collagen, in order to promote HA synthesis in the joint cavity, reduce inflammation, and protect the chondrocytes in an osteoarthritic joint (U.S. Pat. Nos. 6,645,948; 6,476,005).

Scientific evidence clearly demonstrates the efficacy of sulphated GAGs in increasing the HA content in the synovial fluid of patients suffering from inflammatory osteoarthritis (McCarty et al., *Med Hypoth,* 2000, 54:798-802; McCarty M F, *Med Hypoth,* 1998, 50:507-510).

Further patents and patent applications are also known which describe new treatments for inflammatory osteoarthritis involving intra-articular administration of HA in association with chondroitin sulphate (U.S. Pat. No. 6,906,044), or claiming oral treatment with HA at given doses (U.S. Pat. No. 6,607,745), possibly in association with glucosamine, chondroitin sulphate or glucosamine sulphate (U.S. Pat. No. 6,924,273); finally, the use of HA with high molecular weight for the prevention and treatment of osteoporosis is known (patent application WO2005/032276).

In addition to glucosamine sulphate and chondroitin sulphate, another sulphated GAG used for chondroprotection is HA, suitably sulphated as described in the prior art, to which anti-inflammatory, anticoagulant and cell-adhesion-inhibiting effects are attributed.

In particular, US 2004 0,053,885 discloses the use of sulphated hyaluronic acid (subsequently referred to as HA-S) in the intra-articular treatment of inflammatory arthritis, and specifically rheumatoid arthritis (autoimmune disease), while EP 754460 B1 claims the use of HA-S in the parenteral injectable treatment of inflammatory states, including joint rheumatism.

The present invention supersedes the prior art because it relates to formulations based on chemically sulphated HA, for oral administration or intra-articular injection, which effectively slow joint degeneration and promote reconstruction of the extracellular matrix in joints affected by chronic degenerative osteoarthritis, which is consequently not at the inflammatory stage (these compositions therefore cannot be used to treat inflammatory osteoarthritis). According to a particularly preferred aspect, the present invention relates to formulations based on HA chemically modified by sulphation as described in EP 702699 B1: the Applicant has demonstrated the therapeutic efficacy of HA-S by comparison with a standard treatment based on sulphated glycosaminoglycans in the treatment of osteoarthritic cartilage deficiency, and compared its efficacy with non-sulphated HA to demonstrate the clear pharmacological superiority of HA-S over both GAGs and HA.

DETAILED DESCRIPTION OF THE INVENTION

The present invention relates to formulations based on HA chemically modified by sulphation, which are effective in the (preferably oral) treatment of chronic forms of degenerative osteoarthritis without inflammatory sequelae.

As already stated, the process of degenerative osteoarthritis causes progressive damage to the extracellular matrix in the joint cartilage. This damage is manifested by thinning of the matrix and loss of the chondrocyte component; the process culminates with the total destruction of the joint cartilage. The disorder can be manifested as chronicisation of inflammatory osteoarthritis or represent the physiological development of the joint aging process.

From the morphological standpoint the cartilage can be divided into four different zones, from the joint surface to the subchondral bone, namely:
  zone I: the thinnest, outermost part, which is only partly cellularised,
  zone II: the transitional zone, which contains the highest percentage of cells and is basically responsible for matrix production,
  zone III: the radial zone, which is the largest; the entire thickness of the cartilage depends on its structure,
  zone IV: the calcified zone, a thin layer that separates the radial zone from the subchondral bone.

The deeper the zone affected, the more serious is the damage caused by degenerative osteoarthritis. It develops with the same processes, involving the same zones, whether it is due to inflammatory disease or results from physiological joint aging caused by advancing age or overload.

A pharmacological treatment able to provide the extracellular matrix with the "building blocks" it needs to reconstitute its complex structure of proteoglycans, in order to strengthen its load-bearing skeleton and prevent cell loss, would be most useful at the stage of chronicisation of the disorder. This invention demonstrates that the administration of sulphated hyaluronic acid represents a valid therapeutic approach for these purposes because it increases, within the joint, the presence of the material that constitutes the "scaffolding" of the cartilage matrix and, by ensuring its structural integrity, prevents its decellularisation. The formulations of the invention can therefore also be used for the prevention of cartilage damage.

The in vivo trial performed by the Applicant demonstrates that HA-S slows degradation and stimulates regeneration of the basic structure of the extracellular matrix to a surprisingly greater extent than other GAGs and non-sulphated HA.

The sulphated hyaluronic acid suitable for the purpose of this invention is prepared according to a process described in EP 702699 B1: sulphation is performed with the $SO_3$-pyridine complex, and involves the alcoholic hydroxyls present in the polysaccharide chain.

The degree of sulphation can range between 0.5 and 3.5 (EP 0940410 B1), and is preferably between 0.5 and 1.5 (the average grade is defined as 1:1 sulphate group to disaccharide group), starting from HA with different molecular weights, ranging from 50.000 to 800.000 D, preferably 100,000 to 230.000 D, using HA produced by extraction, fermentation or technological means.

The derivative obtained maintains all the physical characteristics of the starting polymer; in particular, the molecular weight of HA is not changed by the sulphation process, consequently allowing the same viscosity as the starting polysaccharide to be maintained.

The experiments described below were conducted by comparing HA-S produced by fermentation, having an average molecular weight of 180/200 KD and an average degree of sulphation of 1, with a reference treatment based on Condral® (galactosaminoglucuronoglycan sulphate, the depolymerised form of chondroitin sulphate) and with a treatment based on HA (with a molecular weight of 180/200 KD) against the untreated control.

Trial Design: Inducement and Treatment of Degenerative Osteoarthritis

The experiments were conducted on adult rabbits, in strict compliance with current legislation, Degenerative osteoarthritis of the right knee was induced unilaterally by surgical resection of the anterior cruciate ligament according to a well-established experimental model (Yoshimi et al., *Clin Orthop Relat Res*, 1994, 298:296-304). The experimental model used does not trigger an inflammatory process, as demonstrated by the total absence of plasma infiltrates in the joint cavities of all the treated animals, including the controls (Table). Surgical ablation of the ligament consequently represents a good example of experimental degenerative osteoarthritis, which allows correct pharmacological evaluation of the formulations tested.

The animals were divided into 4 homogenous groups (6 animals per group) and treated orally, 24 hours after surgery, every day for 61 days, with:
  saline solution 0.9% NaCl (Control);
  HA-S at the dose of 5.5 mg/kg;
  HA at the dose of 20 mg/kg;
  Condral® at the dose of 20 mg/kg.

At the end of the treatment the animals were killed and examined macroscopically to cheek for the absence of systemic toxicity. Next, the lateral and medial condyles of the femur with the tibial plate were fixed in formalin buffered to 10% and embedded in paraffin wax. The preparations were then processed, by a method known to one skilled in the art, to obtain sections analysable under the optical microscope after staining with haematoxylin-eosin.

The cartilage tissue removed from the medial and lateral femoral condyles was then subjected to semiquantitative histopathological analysis and histomorphometric analysis. In particular, parameters relating to degeneration, the structural integrity of the cartilage and the extent of abrasion on the thickness of the cartilage were taken into consideration.

Analysis of Results

TABLE

| Group | Synovial membrane: plasma infiltrates | Cartilage tissue: plasma infiltrates |
|---|---|---|
| Control | 0 | 0 |
| HA-S | 0 | 0 |
| HA | 0 | 0 |
| Condral | 0 | 0 |

As already stated, the total lack of plasma infiltrates in the synovial fluid and the cartilage confirms the complete absence of inflammation in the joint cavity in the controls treated with NaCl and in all the groups studied.

Macroscopic analysis of the animals and their organs also demonstrated the lack of systemic toxicity of the pharmacological compositions tested.

FIG. 1 summarises the data collected from the cartilage examination: in the group of animals treated with saline solution (controls), serious degeneration characterised by morphological alteration of the cell component was evident. The situation of the animals treated with Condral® was better; in this case the cartilage degeneration was estimated at 2.8, and was therefore moderate/marked; it is important to note that this result is very similar to that obtained with HA treatment. The cartilage of the animals treated with HA-S was in a much better situation: the level of degradation was slight (1,7). Oral administration of HA-S therefore proved effective in significantly slowing the process of degradation of the cartilage of joints affected by degenerative osteoarthritis.

Figure 2:
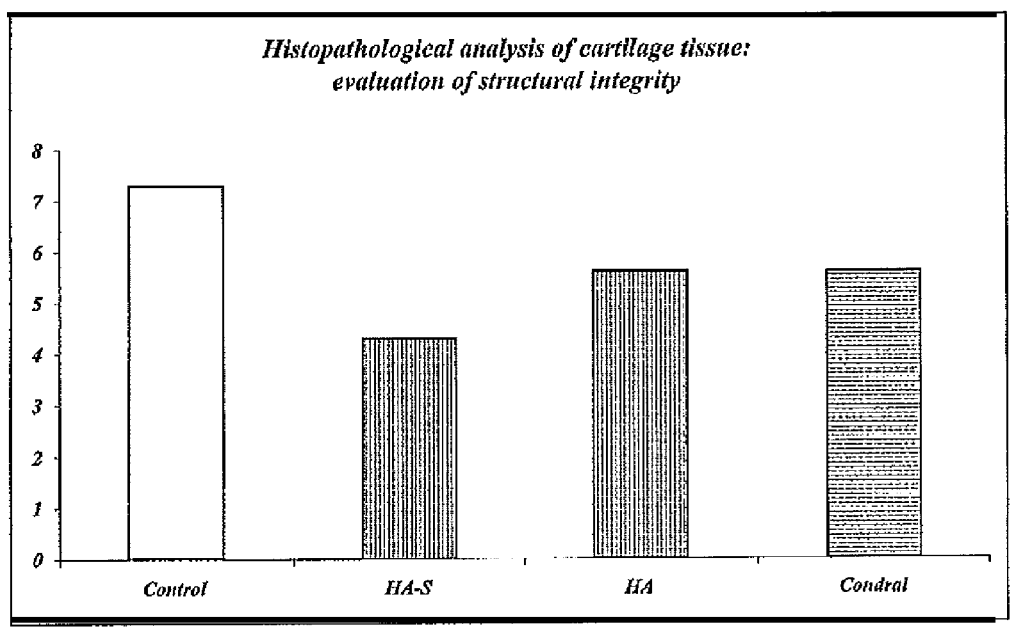

A second, important evaluation relates to analysis of the structural integrity of the cartilage tissue, which is measured, according to recognised standards, in terms of irregularity of the surface and of the cartilage structure (FIG. 2). This graph, like the preceding one, confirms that treatment with HA-S helps to maintain good structural integrity, to a significant extent compared with the controls, and also compared with Condral® treatment. The group of animals treated with HA-S only presented slight cracks in the transitional cartilage zone, whereas those treated with Condral® presented marked lesions of the radial zone; the finding relating to treatment with HA, which again proved as effective as Condral®, is particularly interesting.

Figure 3:
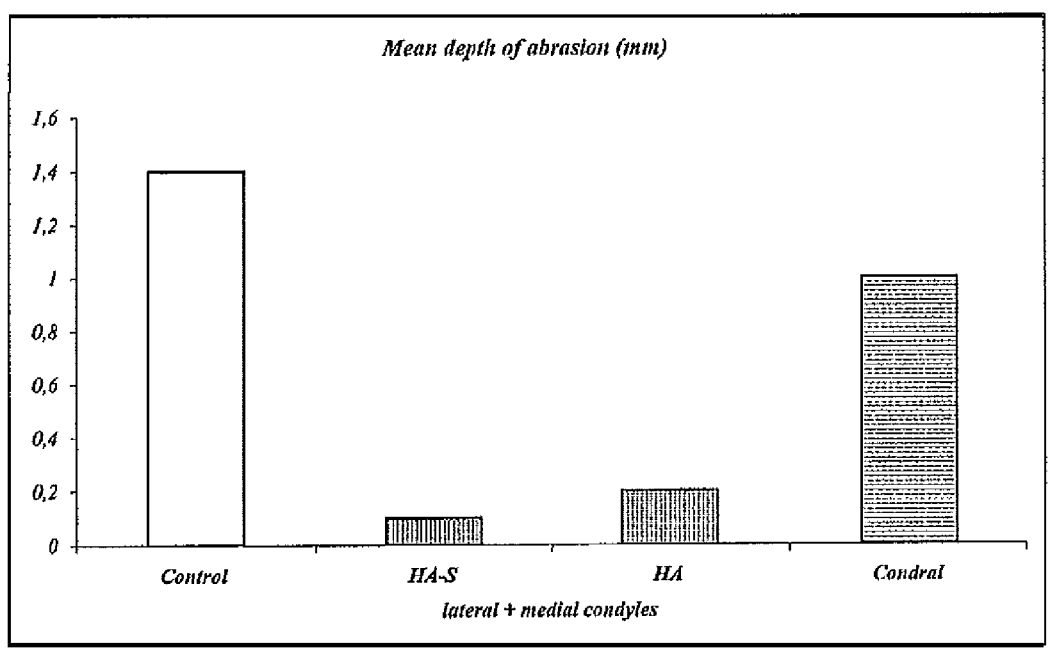

Finally, FIG. 3 illustrates the depth of the lesion along the entire thickness of the cartilage, the maximum lesion being one which causes exposure of bone tissue following total loss of cartilage.

The data illustrate the mean values of the lesions of the lateral and medial condyles; once again it was confirmed that oral treatment with HA-S is more effective than treatment with Condral® or treatment with HA alone in preserving the integrity of the cartilage matrix.

Analysis of the data presented here clearly indicates that HA-S is more effective than sulphated GAGs and HA in the treatment of non-inflammatory osteoarthritis, whether it results from trauma/disease or the normal joint aging process.

If necessary, HA-S could possibly be associated with other molecules useful to strengthen the extracellular matrix, such as collagen (possibly hydrolysed) or other GAGs, or with other pharmacologically and/or biologically active substances such as growth factors and/or hormones, vitamins (especially vitamins A, C, D, and E, and group B in general), antibiotics and mineral salts (especially calcium, magnesium and selenium salts and other trace elements). The procedures described and claimed herein therefore represent a definite improvement on the current oral treatments for the disorder in question.

The surprising results obtained with oral administration of HA-S, and the well-known chemico-physical and pharmacological characteristics of hyaluronic acid derivatives, also suggest the possible administration of these formulations by injection, in particular intra-articular injection, limited to forms of chronic degenerative osteoarthritis in which there are no inflammatory symptoms. In this case too, HA-S could possibly be associated with other molecules such as other GAGs or other pharmacologically and/or biologically active substances such as growth factors and/or hormones, vitamins, antibiotics and antivirals.

Some examples of preparation of the formulations containing HA-S of the invention, for oral and intra-articular administration, are described below by way of example and not of limitation. HA-S can be formulated in all known ways according to the state of the art in association with stabilisers, excipients, preservatives and/or other substance considered useful to obtain the best possible formulation, for the preparation of granulates, suspensions, solutions, capsules and tablets.

Oral Formulations

The HA used in these formulations has an average degree of sulphation of 1, and an average molecular weight of 180/200 KD; the concentration of the Active ingredient ranges between 50 and 400 mg per dose unit.

EXAMPLE 1

HA-S 75 mg Rigid Gelatin Capsule

| Constituent | Amount (mg/cap) |
|---|---|
| Active ingredient: | |
| HA-S | 75 |
| Excipients | |
| Lactose | q.s. for the capacity of the 00 capsule |
| Corn starch | 16.5 |
| Anhydrous colloidal silicon dioxide | 7.7 |
| Magnesium stearate | 3.3 |

Initially mix the HA-S, lactose, corn starch and anhydrous colloidal silicon dioxide. Add magnesium stearate to the premix obtained, and mix. Distribute the final mixture between rigid gelatin capsules format 00.

EXAMPLE 2

HA-S 200 mg Rigid Gelatin Capsule

| Constituent | Amount (mg/cap) |
|---|---|
| Active ingredient: | |
| HA-S | 200 |
| Excipients | |
| Microcrystalline cellulose | q.s. for the capacity of the 00 capsule |
| Corn starch | 35.1 |
| Anhydrous colloidal silicon dioxide | 5 |
| Magnesium stearate | 5 |

Initially mix the HA-S, microcrystalline cellulose, corn starch and anhydrous colloidal silicon dioxide. Add magnesium stearate to the premix obtained, and mix. Distribute the final mixture between rigid gelatin capsules format 00.

EXAMPLE 3

HA-S 400 mg Rigid Gelatin Capsule

| Constituent | Amount (mg/cap) |
|---|---|
| Active ingredient: | |
| HA-S | 400 |
| Excipients | |
| Microcrystalline cellulose | q.s. for the capacity of the 00 capsule |
| Corn starch | 35.1 |
| Anhydrous colloidal silicon dioxide | 5 |
| Magnesium stearate | 5 |

Initially mix the HA-S, microcrystalline cellulose, corn starch and anhydrous colloidal silicon dioxide. Add magnesium stearate to the premix obtained, and mix. Distribute the final mixture between rigid gelatin capsules format 00.

EXAMPLE 4

HA-S 400 mg Granulate

| Constituent | Amount (mg/sachet) |
|---|---|
| Active ingredient: | |
| HA-S | 400 |
| Excipients | |
| Microcrystalline cellulose | 65 |
| Corn starch | 15.5 |
| Sorbitol | 2250 |
| Polyvinylpyrrolidone | 47.5 |
| Citric acid | 10 |
| Aspartame | 32 |
| Orange flavouring | 180 |

Initially mix the HAS1, microcrystalline cellulose and corn starch. Mix with the binder solution consisting of water and polyvinylpyrrolidone. When the mixture is uniformly moist, granulate through a 2 mm sieve. Dry the granulate, then sieve the dried granulate, forcing it through an 0.8 mm sieve. Mix the granulate powder with sorbitol, citric acid, aspartame and orange flavouring. Fill sachets with the granulate.

Injectable Formulations

HA-S grade 1 or 2, having an average molecular weight of 180/200 KD or 500/750 KD, prepared in sterile, pyrogen-free saline solution at the concentration of 1-100 mg/ml, preferably 5-50 mg/ml, and even more preferably 10-20 mg/ml, is preferably used for the injectable intra-articular preparations. The final solution must be sterile and pyrogen-free. It can also be freeze-dried and reconstituted at the time of use.

The invention claimed is:

1. A method for treating cartilage damage caused by degenerative osteoarthritis presenting without plasma infiltrates of cartilage comprising orally administering to a patient in need thereof an effective degenerative osteoarthritis treatment amount of a sulphated hyaluronic acid (HAS), wherein the hyaluronic acid used to prepare said HAS has a molecular weight between 100,000 and 230,000 D, and wherein said HAS has a degree of sulphation between 0.5 and 3.5, and where said administration is effective to increase within a joint exhibiting said cartilage damage the amount of the material that constitutes the scaffolding of the cartilage matrix.

2. A method for treating cartilage damage caused by wear due to aging of a joint structure presenting without plasma infiltrates of cartilage comprising orally administering to a patient in need thereof an effective amount of a sulphated hyaluronic acid (HAS), wherein the hyaluronic acid used to prepare said HAS has a molecular weight between 100,000 and 230,000 D, and wherein said HAS has a degree of sulphation between 0.5 and 3.5, and where said administration is effective to increase within a joint exhibiting said cartilage damage the amount of the material that constitutes the scaffolding of the cartilage matrix.

3. The method according to claim 1 or 2, wherein the degree of sulphation of the sulphated hyaluronic acid is between 0.5 and 1.5.

4. The method according to claim 3, wherein said sulphated hyaluronic acid is administered in an amount between 75 and 400 mg per dose unit.

5. The method according to claim 1 or 2, wherein said oral administration is at a dosage amount of 75-400 mg of said sulphated hyaluronic acid.

6. The method according to claim 1 or 2, wherein the sulphated hyaluronic acid has an average degree of sulphation of 1.0 and the molecular weight of said hyaluronic acid is between 180,000 and 200,000 D.

7. The method according to claim 1 or 2, wherein said sulphated hyaluronic acid is administered in combination with at least one member selected from the group consisting of collagen, hydrolysed collagen, glycosaminoglycans, vitamins, mineral salts, hormones, antibiotics and growth factors.

* * * * *